United States Patent [19]
Sommer et al.

[11] Patent Number: 6,132,456
[45] Date of Patent: Oct. 17, 2000

[54] ARRANGEMENT FOR IMPLANTING AN ENDOCARDIAL CARDIAC LEAD

[75] Inventors: John L. Sommer, Coon Rapids; Michael P. Lodes, Cedar, both of Minn.

[73] Assignee: Medtronic, Inc., Minneapolis, Minn.

[21] Appl. No.: 09/041,073

[22] Filed: Mar. 10, 1998

[51] Int. Cl.[7] ...................................................... A61N 1/05
[52] U.S. Cl. .......................... 607/127; 607/119; 606/129; 600/585
[58] Field of Search ..................................... 607/119, 122, 607/125–128, 116; 600/374, 375, 585; 606/129, 108

[56] References Cited

U.S. PATENT DOCUMENTS

| | | |
|---|---|---|
| 3,348,548 | 10/1967 | Cardack . |
| 3,788,329 | 1/1974 | Friedman . |
| 4,646,755 | 3/1987 | Kane . |
| 4,876,109 | 10/1989 | Mayer et al. . |
| 4,972,847 | 11/1990 | Dutcher et al. . |
| 5,003,990 | 4/1991 | Osypka . |
| 5,007,435 | 4/1991 | Doan et al. . |
| 5,036,854 | 8/1991 | Schollmeyer et al. . |
| 5,046,497 | 9/1991 | Millar . |
| 5,139,033 | 8/1992 | Everett et al. . |
| 5,246,014 | 9/1993 | Williams et al. . |
| 5,304,218 | 4/1994 | Alferness . |
| 5,531,783 | 7/1996 | Giele et al. . |
| 5,545,200 | 8/1996 | West et al. . |
| 5,639,276 | 6/1997 | Weinstock et al. ..................... 607/122 |

*Primary Examiner*—George R. Evanisko
*Attorney, Agent, or Firm*—Reed A. Duthler; Harold R. Patton

[57] ABSTRACT

An arrangement for transvenously introducing and fixing a cardiac electrode at a cardiac implantation site. The arrangement includes a pusher having an elongated body of flexible material, which may be coupled with a cardiac lead adjacent the distal end of the cardiac lead and may be employed to advance the cardiac lead transvenously. The pusher is provided with an engagement mechanism which engages the distal end of the cardiac lead while the lead extends proximally along side the exterior surface of the pusher and which engages the distal end of the lead body when the pusher body is advanced distally and disengages from the cardiac lead body when the pusher is withdrawn proximally. The pusher body has sufficient column strength to be advanced through a patient's venous system to a desired implantation site within the heart. The cardiac lead may include a fixation helix extending from the distal end of the lead and the pusher body may be employed to apply torque to the distal end of the lead to screw the helix into cardiac tissue at a desired implantation site.

21 Claims, 9 Drawing Sheets

ARRANGEMENT FOR IMPLANTING AN ENDOCARDIAL CARDIAC LEAD

FIELD OF THE INVENTION

The present invention relates to endocardial implantable cardiac leads for applying electrical stimulation to and/or sensing electrical activity of the heart at one or more electrode positioned at a cardiac implantation site within a heart chamber or cardiac vessel adjacent a heart chamber and more particularly to an arrangement for transvenously introducing and fixing the electrode at the implantation site

BACKGROUND OF THE INVENTION

Implantable medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, endocardial leads are placed through a transvenous route to locate one or more sensing and/or stimulation electrode along or at the distal end of the lead in a desired location in a chamber of the heart or a blood vessel of the heart. In order to achieve reliable sensing of the cardiac electrogram and/or to apply stimulation that effectively paces or cardioverts the heart chamber, it is necessary to accurately position the electrode surface against the endocardium or within the myocardium at the cardiac implantation site and fix it during an acute post-operative phase until fibrous tissue growth occurs.

The pacemaker or defibrillator implantable pulse generator (IPG) or the monitor is typically coupled to the heart through one or more of such endocardial leads. The proximal end of such leads typically is formed with a connector which connects to a terminal of the IPG or monitor. The lead body typically comprises one or more insulated conductive wire surrounded by an insulating outer sleeve. Each conductive wire couples a proximal lead connector element with a distal stimulation and/or sensing electrode. An endocardial cardiac lead having a single stimulation and/or sensing electrode at the distal end and a single conductive wire is referred to as a unipolar lead. An endocardial cardiac lead having two or more stimulation and/or sensing electrodes at the distal end and two or more conductive wires is referred to as a bipolar lead or a multi-polar lead, respectively.

In order to implant an endocardial lead within a heart chamber, a transvenous approach is utilized wherein the lead is inserted into and passed through the subclavian, jugular, or cephalic vein and through the superior vena cava into the right atrium or ventricle. An active or passive fixation mechanism is incorporated into the distal end of the endocardial lead and deployed to maintain the distal end electrode in contact with the endocardium position. Considerable effort has been undertaken to develop electrode passive and active fixation mechanisms that are simple to use and are reliable. Passive fixation mechanisms do not invade the myocardium but cooperate with cardiac tissue or structures to locate the electrode against the endocardium. The most successful passive fixation mechanism comprises a plurality of soft, pliant tines that bear against cardiac structure surfaces, e.g. the trabeculae in the right ventricle and the atrial appendage, to urge the distal tip electrode against the endocardium. Active fixation mechanisms are designed to penetrate the endocardial surface and lodge in the myocardium without perforating through the epicardium or into an adjoining chamber. The most widely used active fixation mechanism employs a sharpened helix, which typically also constitutes the distal tip electrode. Typically, some sort of shroud or retraction mechanism is provided to shield the helix during the transvenous advancement into the desired heart chamber from which the helix can be advanced and rotated when the desired cardiac implantation site is reached to effect a penetrating, screw-in fixation. In one manner or another, the helix is adapted to be rotated by some means from the proximal end of the lead outside the body in order to screw the helix into the myocardium and permanently fix the electrode.

More recently, endocardial pacing and cardioversion/defibrillation leads have been developed that are adapted to be advanced into the coronary sinus and coronary veins branching therefrom in order to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at the cardiac implantation site.

The heart beats approximately 100,000 times per day or over 30 million times a year, and each beat stresses at least the distal end portion of the lead. Over the years of implantation, the lead conductors and insulation are subjected to cumulative mechanical stresses, as well as material reactions as described below, that can result in degradation of the insulation or fractures of the lead conductors with untoward effects on device performance and patient well being. The endocardial lead body is subjected to continuous stretching and flexing as the heart contracts and relaxes and is formed to be highly flexible and durable. It is necessary to temporarily stiffen the lead conductor sire to advance the lead through these blood vessels and to locate the distal electrode(s) at the cardiac implantation site.

Early implantable, endocardial and epicardial, bipolar cardiac pacing leads of the type disclosed in U.S. Pat. No. 3,348,548 placed the separate coiled wire conductors in a side by side configuration and incorporated a lumen for receiving a stiffening stylet inside the lumen of at least one of the conductor coils. This design was replaced by a coaxial configuration of the type shown in U.S. Pat. No. 3,788,329 wherein the separate coiled wire conductors are wound in differing diameters separated from one another by tubular insulating sheaths and extend coaxially about a central lumen for receiving the stiffening stylet. The stiffening wire body during the transvenous introduction. Most current endocardial cardiac leads employ multi-filar, parallel-wound, coiled wire conductors electrically connected in common in an electrically redundant fashion as a single polarity lead conductor in each of the unipolar, bipolar and multi-polar lead configurations. Such redundant coiled wire conductors of bipolar and multi-polar lead bodies are coaxially arranged about the stiffening stylet receiving lumen and insulated from one another by coaxially arranged insulating sheaths separating each coiled wire conductor from the adjacent coiled wire conductor(s).

In the implantation of a cardiac device of the types listed above, and in the replacement of previously implanted cardiac leads, two or more transvenous cardiac leads are typically introduced through the venous system into the right chambers or coronary sinus of the heart. It has long been desired to minimize the diameter of the transvenous cardiac lead body to facilitate the introduction of several cardiac leads by the same transvenous approach. Moreover, a number of multi-polar, endocardial cardiac leads have been designed to accommodate more than two electrodes or to make electrical connection with other components, e.g., blood pressure sensors, temperature sensors, pH sensors, or the like, in the distal portion of the lead. The increased number of separate polarity coiled wire conductors is difficult to accommodate in the conventional coaxial coiled wire conductor winding arrangement employing tubular insulating sheaths to separate the coil wire conductors of differing diameters having a desired overall lead body outer diameter.

This need for increased numbers of lead conductors in the lead body has led to the development of separately insulated, coiled wire conductors that are parallelwound with a common diameter and are separately coupled between a proximal connector element and to a distal electrode or terminal in the manner described in commonly assigned U.S. Pat. No. 5,007,435, for example, incorporated herein by reference. The coaxial construction technique may also be combined with the parallel-winding technique to multiply the total number of separate coiled wire conductors accommodated within a specified endocardial lead body outer diameter.

All of the above considerations as to the complexity of the leads, the number of leads implanted in a common path and the advancement of coronary sinus leads deep in the coronary veins have led to efforts to at least not increase and optimally to decrease the overall diameter of the cardiac lead body without sacrificing reliability and usability. More recently, it has been proposed to diminish the lead body further by eliminating the lumen for receiving the stiffening stylet and by replacing the coiled wire conductor with highly conductive stranded filament wires or cables. In bipolar or multi-polar leads, each such cable extends through a separate lumen of the lead body to maintain electrical isolation. Without the stiffening stylet, it is necessary to resort to use of another mechanism to pass the lead through the vessel paths identified above and to position and fix the distal end electrode of the lead at the cardiac implantation site in the heart chamber or cardiac blood vessel.

One approach for implantation of small diameter endocardial screw-in leads is disclosed in commonly assigned U.S. Pat. No. 5,246,014, incorporated herein by reference, that employs a highly flexible, introducer catheter surrounding the lead body and engaging a distal screw-in electrode. The assembled introducer catheter and cardiac lead are advanced to the cardiac implantation site and rotated to screw the distal screw-in electrode into the myocardium of the right atrium or ventricle. The introducer it then retracted proximally over the lead body and proximal connector end assembly. The introducer can also be used to direct a cardiac lead into the coronary sinus opening, but it is difficult to advance the introducer and lead deep within the coronary sinus and branching veins.

Another difficulty with use of such an introducer surrounding the cardiac lead is that permanently implantable endocardial leads are formed typically with a proximal connector end assembly having a diameter exceeding that of the lead body and conforming to an industry standard so that the connector end assembly can be fitted into and seal with an IPG connector bore conforming to the same standard. Consequently, the introducer has to be made large enough to fit over the enlarged diameter connector end assembly. This detracts from the ability to advance the introducer and lead assembly through small diameter blood vessels. Or the lead has to be made with a small diameter, non-conforming, connector end assembly or without any connector end assembly and therefore requiring connection to an adapter to be made conforming to the standard. This is inconvenient and can result in a diminished reliability.

Another approach is disclosed in U.S. Pat. No. 5,003,990, also incorporated by reference herein, that relies on a guidewire and a carriage that releasably engages the distal screw-in electrode and is pushed along the guidewire as the lead body is pushed along the transvenous path. The guidewire is first introduced along one of the above-described desired paths, and the carriage engaging the distal electrode is placed over the proximal end of the guidewire and introduced into the blood vessel. Force is exerted against the lead body to push the carriage and the distal end of the lead body distally along the guidewire until the distal electrode is near to the cardiac implantation site. The guidewire end or a curve in its distal end is engaged by the carriage, and the lead body distal end is bent until the screw-in electrode disengages from the carriage. Then, the carriage is retracted along the guidewire by pulling on another wire attached to the carriage or by the retraction of the guidewire, and the lead body is rotated from the proximal end to screw the helix electrode into the myocardium. Such retraction of the relatively bulky carriage presents the possibility of damage to an artery or vein by the carriage. In addition, releasing the carriage from the guidewire requires the lead or catheter to be bent in the area of the carriage presenting further possibilities of tissue damage during such carriage removal. Still further, once the lead is free of the carriage, its distal end will not necessarily be at its desired final implantation position. Use of the carriage during both implantation of the lead or catheter and retraction of the carriage requires numerous manipulations by the physician which only adds further complexity to an already complex procedure.

In a further approach disclosed in U.S. Pat. No. 5,304,218, incorporated by reference herein, a cardiac lead is formed with a channel in the distal tip that receives a guidewire that has already been advanced through the path to the cardiac implantation site. The lead is pushed over the guidewire to the cardiac implantation site where the guidewire is withdrawn and the lead is either fixed in place or left at the cardiac implantation site. There is no disclosure of how this approach could be used to advance a cardiac lead having an active or passive fixation mechanism at or near the channel in the distal end of the lead body.

Moreover, in both of these approaches, the lead body must possess sufficient column strength to allow it (as well as the carriage of the '990 patent) to be pushed from the proximal end outside the patient's body and along the guidewire. The lead body diameter and/or construction materials that are required in order to make the lead body stiff enough to accomplish this over the wire advancement method necessarily make the lead body larger and less flexible than is desirable to withstand the rigors of chronic flexing as described above. The over the wire approach is classically employed in advancement of balloon catheters for PTCA use which is intended to be of short duration.

Thus, a need remains for an introduction arrangement that allows the introduction of an endocardial cardiac lead having a highly flexible lead body and small lead body diameter into a heart chamber or vein and allowing the use of the active or passive fixation mechanism (if present) at the cardiac implantation site.

SUMMARY OF THE INVENTION

It is therefore an object of the present invention to provide an introduction arrangement that can be employed to introduce an endocardial cardiac lead that lacks a lumen for receiving a stiffening stylet and lacks sufficient column strength to be pushed to a cardiac implantation site of a cardiac lead electrode in a heart chamber or cardiac blood vessel.

It is a particular object of the present invention to provide such an arrangement that enables the advancement of the distal lead end or such a cardiac lead through a convoluted path into a heart chamber or within small diameter cardiac veins and to release the distal lead end therein with the cardiac electrode(s) at a selected cardiac stimulation site(s). Preferably, the cardiac implantation sites include the right atrium, the right ventricle, the coronary sinus and/or the great vein and branch veins alongside the left ventricle.

It is a further particular object of the present invention to provide such an arrangement that enables the advancement of the distal lead end having an active fixation helix to the cardiac implantation site, the rotation of the helix to screw it into the myocardium and the release of the distal lead end after the helix is fixed to the myocardium to thereby locate the cardiac lead electrode(s) at a selected cardiac stimulation site(s).

These and other objects of the invention are realized in an arrangement to facilitate the introduction and advancement of an endocardial cardiac lead transvenously within a patient's body to position a cardiac electrode at the cardiac implantation site. The lead includes a lead body extending between a lead connector end assembly at a proximal lead end and at least one cardiac electrode at or adjacent the distal lead end. At least one lead conductor extends within the lead body and is connected at the proximal lead end with the lead connector end assembly and at the distal lead end with the at least one cardiac electrode.

The arrangement preferably comprises an elongated pusher means formed of an elongated pusher body of flexible material that extends between a proximal pusher body end having a pusher body handle affixed thereto and a distal pusher body end. The distal pusher body end is coupled with cardiac lead engaging means for engaging the cardiac lead at or adjacent the distal lead end to advance the distal lead end when the pusher body is advanced and for disengaging from the cardiac lead when the pusher body is withdrawn. The pusher body is fabricated with sufficient column strength to be advanced and to push the cardiac lead distal end along the predetermined transvenous path and through the heart chambers and cardiac blood vessels with the cardiac lead body extending alongside the pusher body. In a preferred embodiment, the pusher body is rod or wire shaped and is preferably formed of a torque cable formed of two coaxial wire coils wound in opposite winding directions. The outer wire coil can be left uncoated or can be coated with an elastomeric compound to control its stiffness and wetability for ease of introduction through the transvenous path and the cardiac blood vessels.

The cardiac lead engaging means extends distally from the distal pusher body end and engages cooperative engagement means at the distal lead end such that the lead body is advanced distally through the transvenous path and to the cardiac implantation site in the heart chamber or cardiac blood vessel as force is applied to the proximal pusher end extending outside the incision in the patient's body. The cardiac lead engaging means is configured to disengage from the cooperative engagement means at the distal lead end simply upon withdrawal of the pusher body.

In a preferred embodiment, the cardiac lead engaging means is a tubular sleeve attached at a proximal sleeve end with the distal pusher body end, the tubular sleeve having a side wall extending between a proximal sleeve side wall lumen opening in the side wall and a distal sleeve lumen end opening. The tubular sleeve side wall surrounds a sleeve lumen for receiving the distal lead end. The tubular sleeve is formed with an insertion slot or breech extending between the proximal sleeve side wall lumen opening and the distal sleeve lumen end opening that is wide enough with respect to the diameter of the lead body or can be stretched wide enough to allow the lead body proximal to the distal lead end to be laterally inserted therethrough, leaving the distal lead end including any fixation mechanism extending distally from the distal sleeve lumen end opening.

The tubular sleeve further comprises a lead retention slot extending proximally in the sleeve side wall from the distal sleeve lumen end opening that engages a cooperative engagement member or key of the distal lead end. After the lead body is laterally inserted through the breach and is within the sleeve lumen, the cooperative engagement member of the distal lead end are aligned. At least a proximal portion of the distal lead end is seated in the tubular sleeve lumen by retracting the lead body proximally through the proximal sleeve side wall lumen opening and inserting the cooperative engagement member into the lead retention slot. The mutual engagement prevents the distal lead end from being released laterally through the breech or from retracting further into the tubular sleeve during advancement of the pusher body. The engagement of the cooperative engagement member in the lead retention slot also allows the distal lead end to be rotated by rotation of the pusher body and the lead body by manipulation of the pusher body handle and lead body extending outside the incision in the patient's skin. The disengagement of the cooperative engagement member from the lead retention slot can be effected by simply retracting the pusher body handle outside the incision.

The cardiac lead body is preferably retained alongside the pusher body by one or more lead retainer located along the length of and fixed to the pusher body, each lead retainer having a lead body receiving slot that is dimensioned with respect to the lead body diameter to receive and loosely retain the lead body alongside the pusher body during advancement through the transvenous path. The lead retainer facilitates the twisting and rotation of the cooperative arrangement of the pusher means and the cardiac lead. After the cardiac electrode(s) are located at the cardiac implantation site, the pusher body is withdrawn proximally and each lead body receiving slot slides along the lead body. The lead body is laterally withdrawn from each lead body receiving slot by the physician when each lead retainer is withdrawn from the skin incision.

In a first preferred embodiment, the endocardial lead further comprises an active fixation mechanism that engages with the retention slot when the distal lead end is inserted into the sleeve lumen and seated therein. Preferably, the active fixation mechanism is a helix that may be the distal cardiac electrode and is intended to be screwed into the myocardium at the cardiac implantation site to retain the electrode in that position. In this embodiment, a radially extending helix shank can be configured to extend into the retention slot. After the distal lead end is seated, and the arrangement is advanced to the implantation site, the entire arrangement is rotated from the proximal lead body end and the proximal pusher body handle extending outside the patient's body to screw the helix into the myocardium. Then, the sleeve and pusher body is retracted over the lead body through the transvenous path and from the incision, and the lead body is withdrawn from the lead body receiving slots of the lead retainers.

In a further preferred embodiment, the cardiac lead is intended to be advanced into the ostium of the coronary sinus and to a cardiac implantation site in the cardiac veins accessed by the coronary sinus to position an electrode(s) adjacent to the right or left atrium or adjacent to the left ventricle. In this embodiment, the coronary sinus lead does not possess any fixation mechanism and relies on the close confinement and low blood flow within these relatively small diameter cardiac leads to remain in place. The distal lead end is configured with the cooperative engagement member that is engaged in the lead retention slot during advancement of the electrode to the cardiac implantation site. After the distal lead end is seated, and the arrangement is advanced to the implantation site, the sleeve and pusher body is retracted over the lead body through the transvenous path and from the incision, and the lead body is withdrawn from the lead body receiving slots of the lead retainers.

The arrangement of the present invention advantageously provides a simplified apparatus for and method of introducing endocardial cardiac leads which lack a lumen for receiving a stiffening stylet and lack sufficient column strength to be pushed to a desired cardiac implantation site.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

The drawing figures are not necessarily to scale.

DETAILED DESCRIPTION OF THE PREFERRED EMBODIMENTS OF THE INVENTION

In the following detailed description, references are made to illustrative embodiments for carrying out the invention. It is understood that other embodiments may be utilized without departing from the scope of the invention. The invention and its preferred embodiment may be implemented in unipolar, bipolar or multi-polar, endocardial, cardiac pacing or monitoring leads having one or more pace/sense electrode(s) or sense electrode(s), respectively, at or adjacent the distal lead end. Similarly, the invention and its preferred embodiment may be implemented in endocardial cardiac defibrillation/cardioversion leads including at least one cardioversion/defibrillation electrode and optionally including one or more pace/sense electrode(s) at or adjacent the distal lead end. Moreover, other sensors for sensing a physiologic parameter may be incorporated into the lead body. Each such pace/sense electrode, sense electrode, cardioversion/defibrillation electrode and sensor is coupled with an insulated electrical conductor extending proximally through the lead body to a proximal lead end connector end assembly. The proximal connector end assembly is adapted to be coupled to the connector terminals of an implantable or external medical device, including an external or implantable pulse generator (IPG) for pacing, cardioversion/defibrillation or both or an external or implantable monitor. Therefore, it will be understood that the arrangement for introduction of an endocardial cardiac lead of the present invention can be employed to introduce permanently implantable and temporary cardiac leads of these types.

The arrangement of the present invention is particularly useful in introducing such endocardial cardiac leads which are quite small in lead body diameter and are so flexible and possess such low column strength that the distal lead end cannot be advanced transvenously and positioned at the desired implantation site without assistance. Moreover, one particular use of the arrangement of the present invention is to introduce such endocardial cardiac leads that are formed using stranded wire conductor(s) within a lead body diameter of about 0.010–026 inches of the type described in the above-incorporated, commonly assigned, '014 patent. The lead body outer diameter is minimized by use of such conductors and by eliminating the lumen for receiving a stiffening stylet. However, the arrangement of the present invention can also be employed to introduce endocardial cardiac leads that employ coiled wire conductors with or without a lumen for receiving a stiffening stylet. In the latter case, the stiffening stylet need not be used to achieve the introduction.

Figure 1:
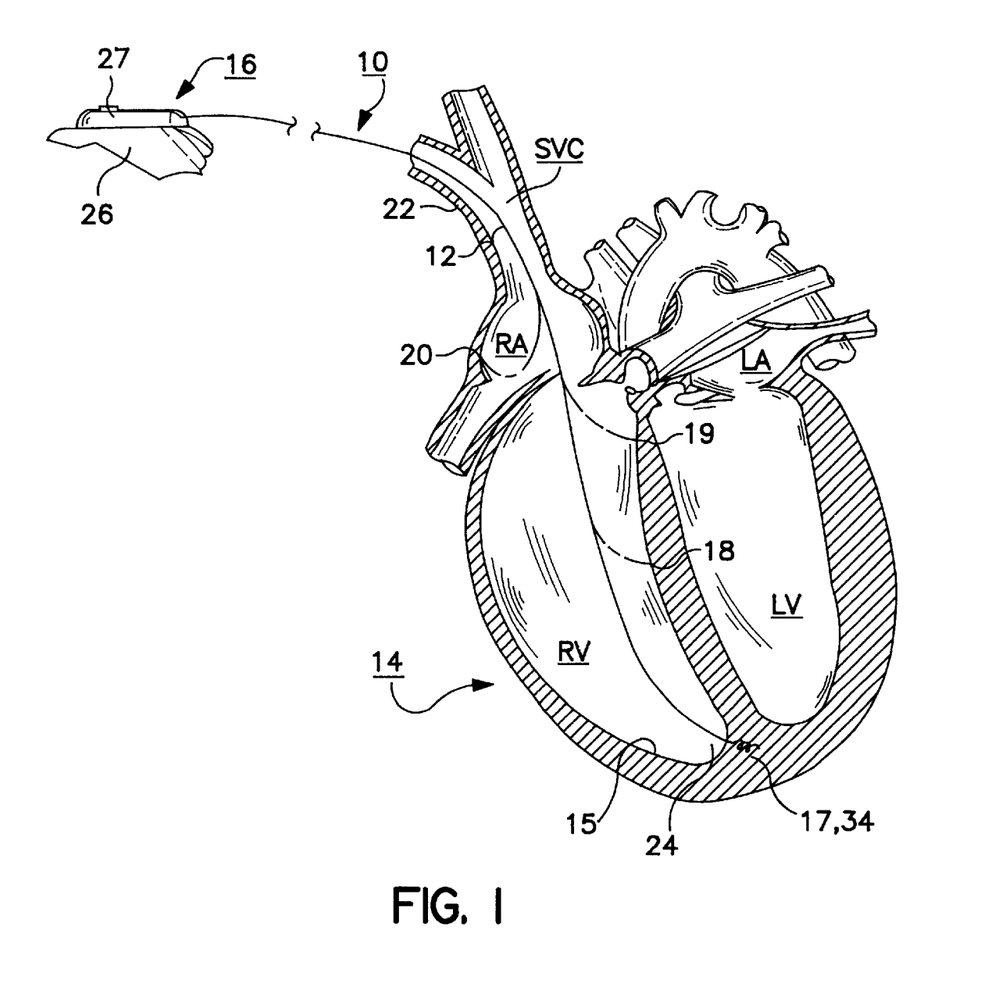
FIG. 1 is a schematic representation of a right heart endocardial cardiac lead bearing at least one cardiac electrode introduced into one of several illustrated cardiac implantation sites of the right heart chambers and coupled at the proximal lead connector end to an implantable medical device.
Figure 2:
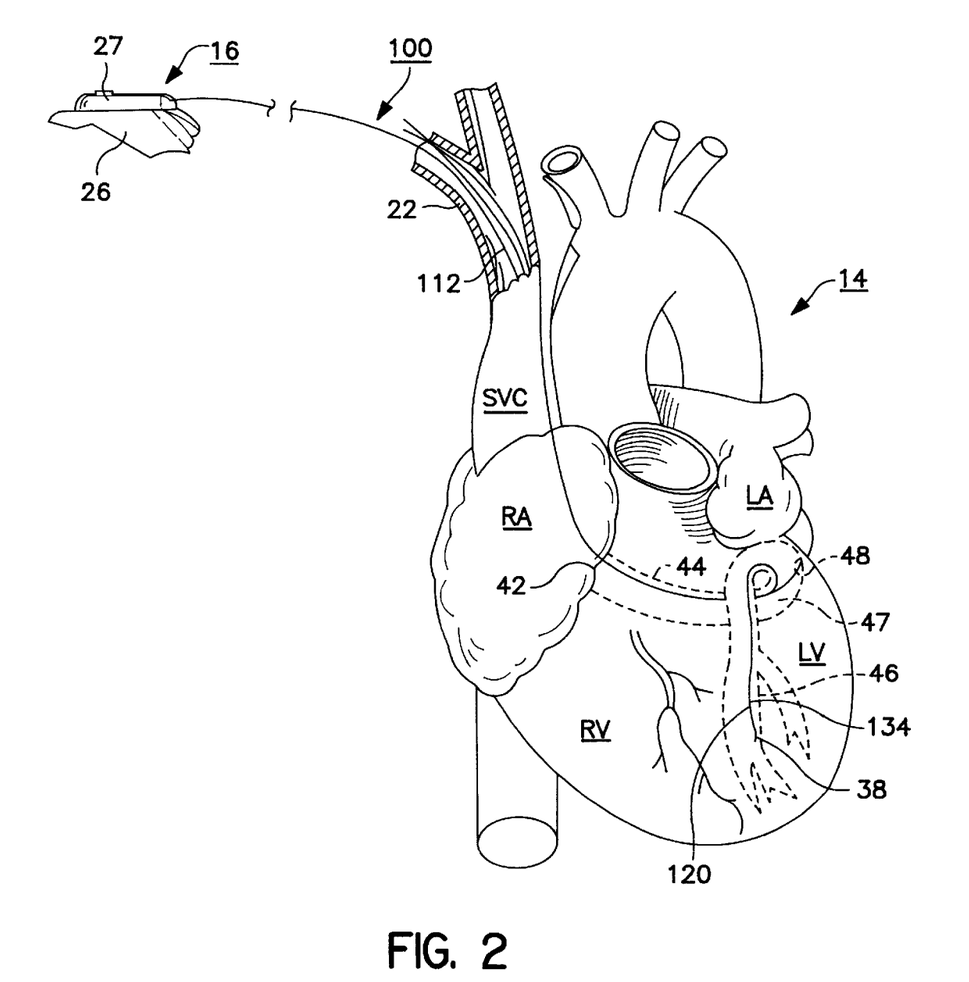
FIG. 2 is a schematic representation of a coronary sinus endocardial cardiac lead bearing at least one cardiac electrode introduced into one possible cardiac implantation sites within the great vein adjacent to left heart chambers and coupled at the proximal lead connector end to an implantable medical device.

FIGS. 1 and 2 are schematic representations of types of right heart cardiac leads 10 (including 10' and 10" described below) and coronary sinus (CS) leads 100 bearing such electrodes introduced into cardiac implantation sites in cardiac blood vessels or chambers of the heart 14 and coupled in each instance at the proximal lead connector ends to an implantable medical device (IMD) 16 of any of the above noted types. In FIGS. 1 and 2, heart 10 includes the upper heart chambers, the right atrium (RA) and left atrium (LA), and the lower heart chambers, the right ventricle (RV), and the left ventricle (LV). The coronary sinus (CS) is also depicted schematically in FIG. 2 extending from the opening 42 in the RA and extending laterally around the atria as the great vein 44 and into the anterior interventricular vein 46 descending inferiorly alongside the RV.

The IMD 16 (depicted partially) is implanted subcutaneously, i.e., below the skin, and includes electronic components and a power supply enclosed with a housing 26 and a connector block 27 having bores for receiving the proximal connector end assembly of the right heart cardiac leads 10 and the CS cardiac lead 100. These figures illustrate some of the possible cardiac implantation sites and routes of introduction of cardiac electrodes on cardiac leads 10 and 100 to the cardiac implantation sites in accordance with the method and apparatus of the present invention. It will be understood that the illustrated cardiac leads 10 and 100 may be used in combination in the heart 14 and/or more than one cardiac lead 10 may be employed. The cardiac leads 10 and 100 of FIGS. 1 and 2 depict possible cardiac implantation sites for single and dual chamber cardiac stimulation and/or sensing depending on the nature of the IMD 16. The illustrated cardiac leads 10 and 100 can be unipolar, bipolar or multi-polar leads and can be fabricated with pace/sense and/or cardioversion/defibrillation electrodes. Alternatively, the cardiac leads can simply bear EGM sensing electrodes and/or physiologic sensors. The present invention is related to introduction arrangement and methods for introducing a cardiac electrode and/or physiologic sensor to one of the illustrated sites and other suitable cardiac implantation sites.

In this regard, the right heart cardiac lead 10 is shown in FIG. 1 extending through the superior vena cava (SVC) 22 inferiorly through the RA and RV and lodging a distal electrode and fixation mechanism into the apex 24 of the heart 14. The lead 10 can include a passive fixation mechanism, e.g., a plurality of soft, pliant tines for engaging in interstices of the trabeculae of the RA and RV and holding a distal cardiac electrode 34 against the endocardium 15. Alternatively, and as shown in detail hereafter, the fixation mechanism and the distal cardiac electrode 34 can be combined in a distally extending helix 17 that is adapted to be screwed into the myocardium and provides active fixation therewith in the manner described in the above-incorporated, commonly assigned, '014 patent from which FIG. 1 is taken. The active fixation helix 17 is typically shrouded in a wide variety of manners during introduction through the vasculature to the cardiac implantation site to prevent the sharpened tip of the helix 17 from snagging or penetrating blood vessels. For example, the helix 17 can be covered with a soluble covering of the type described in U.S. Pat. Nos. 5,531,783 and 4,876,109, incorporated herein by reference. Once soluble coating dissolves in blood over a time period that allows the distal lead end to be advanced to a cardiac implantation site. After dissolution is complete, the exposed helical turns of helix 17 are screwed into the myocardium at cardiac implantation sites where the myocardium is thick enough to avoid penetration of the helix 17 entirely through the septum or heart chamber wall.

FIG. 1 illustrates that the helix 17 can also be affixed to other implantation sites 19 and 18 in the septum between the RV and LV chambers or that it can be attached to relatively thicker areas of the RA, e.g., the exterior atrial wall site 20 through use of the introduction arrangement and method of the present invention. It will also be understood that the helix 17 can also simply attach the distal end of the cardiac lead 10 to the depicted implantation sites 18, 19, 20 and 24 of the RV and RA and a separate cardiac electrode 34 can be provided.

FIG. 2 illustrates the introduction of a straight CS unipolar or bipolar or multi-polar cardiac lead 100 through the SVC and RA chamber and the ostium of the CS to extend alongside the LA chamber and the LV chamber. The CS cardiac lead 100 is formed with an in-line connector end assembly fitting into a bore of IMD connector block 27 in a conventional manner to couple one or more electrically insulated conductors within the lead body with one or more distal CS cardiac electrode 134. The distal CS electrode(s) 134 can be located as depicted deep within the anterior interventricular vein 46 at LV implantation site 38 adjacent to the LV for LV stimulation and/or sensing applications. For LA stimulation and/or sensing applications, the distal CS electrode(s) can be located in the great vein 47 at an implantation site 48 adjacent to the LA. The CS electrode(s) 117 are typically ring shaped and are located proximally to a distal tapered lead extension 120. The LA and LV CS leads typically do not have any distal fixation mechanism and instead rely upon the close confinement and lead body column strength to counter the relatively slow blood flow in the CS and great vein, respectively, and to maintain their cardiac electrode(s) at the cardiac implantation site(s) in the cardiac veins.

Figure 3:
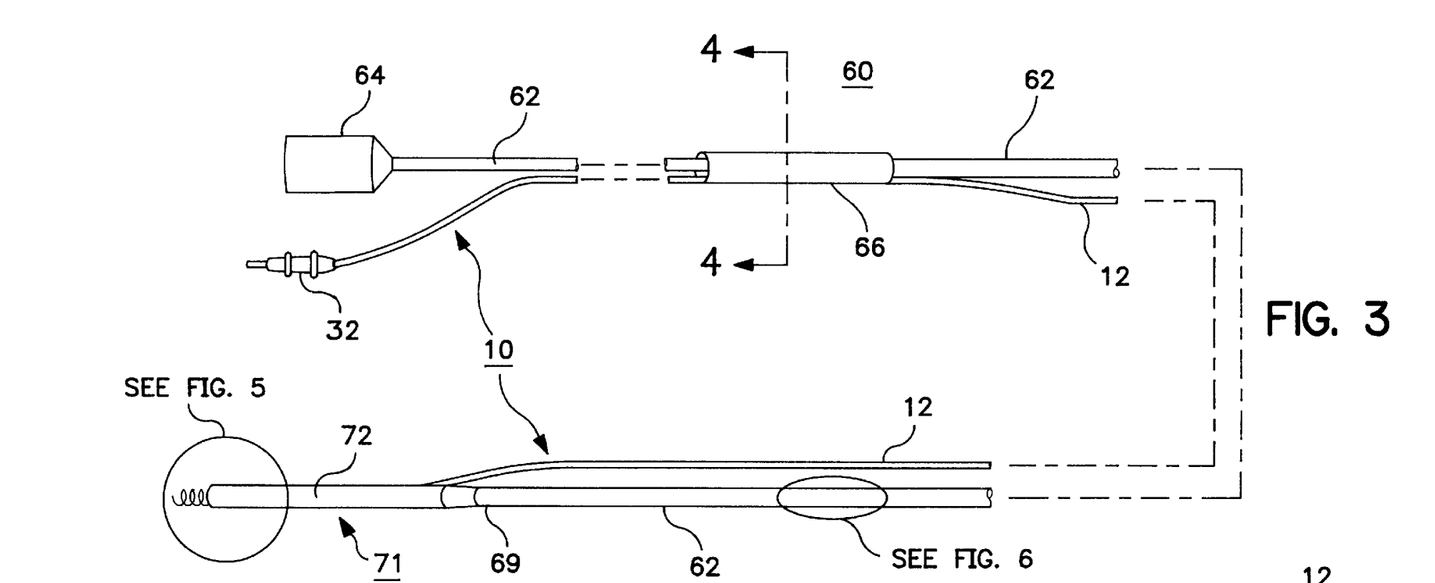
FIG. 3 is a plan view of the introduction arrangement of a first embodiment of the invention for introducing an endocardial cardiac lead of the type illustrated in FIG. 1 into a heart chamber and for attaching an attachment mechanism of the lead to an implantation site in the heart chamber.

Typically, cardiac leads 10 and 100 are implanted in the prior art employing stiffening stylets or introducer catheters or other tools as described in detail above. FIG. 3 is a plan view of the introduction arrangement of a first embodiment of the invention for introducing an endocardial cardiac lead 10 of the type illustrated in FIG. 1 into a right heart chamber and for attaching a fixation mechanism (e.g. helix 17 of FIG. 1) of the lead 10 to the myocardium or endocardium at one of the implantation sites 18, 19, 20, 24, etc., using the lead pusher 60. The arrangement of the lead pusher 60 and lead body facilitates the introduction and advancement of the endocardial cardiac lead 10 transvenously through an incision in the skin and within a patient's body to position the cardiac electrode at the cardiac implantation site.

In the first embodiment, cardiac lead 10, illustrated in FIGS. 1 and 3, includes a lead body 12 having a constant lead body diameter extending between a conventional proximal lead connector end assembly 32 and a distal lead end 33. A stranded wire lead conductor 13 (FIG. 4) extends within the lead body 12 between the proximal connector end assembly 32 and the distal lead end 33. In this embodiment, the distal end of the lead conductor 13 is electrically connected with the active fixation helix 17 at an enlarged crimping zone 35 thereby making it a helical cardiac electrode 34. The helical cardiac electrode 34 constitutes part of the distal lead end 33 and extends distally to a sharpened tip that can be advanced into the myocardium.

The lead pusher 60 comprises an elongated pusher body 62 which has a pusher body exterior surface and extends between a proximal pusher body end having a pusher handle 64 attached thereto and a distal pusher body end 69. The pusher body 62 is formed of flexible material having sufficient column strength to be advanced and to push the cardiac lead distal end 33 along the predetermined transvenous path and through the heart chambers and cardiac blood vessels as shown in FIGS. 1 and 2 with the cardiac lead body 12 extending alongside the pusher body exterior surface.

Figure 6:
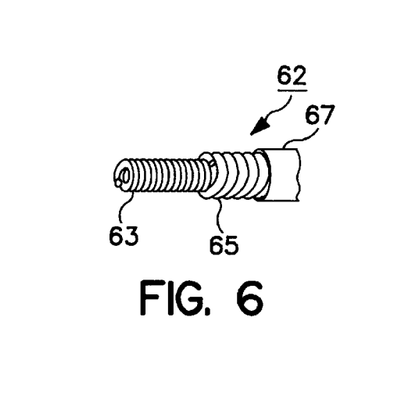
FIG. 6 is an enlarged, partial section view of the distal end of the pusher body of the lead pusher of FIG. 3.

The pusher body 62 is rod or wire shaped and can be a simple, solid metal, stylet wire body having a relatively small outer diameter or can be of more complex construction. FIG. 6 is a detailed view of an alternative construction of the pusher body 62 providing torque transmission capability and column strength for advancing the cardiac lead to the cardiac implantation site. In this embodiment, the pusher body 62 and is formed of a torque cable formed of two coaxial wire coils 63 and 65 wound in opposite winding directions. The outer wire coil 65 can be left uncoated or can be coated with an elastomeric compound in a sheath 67 to control the stiffness and wetability of the pusher body 62 for ease of introduction through the transvenous path and the cardiac blood vessels.

Figure 5:
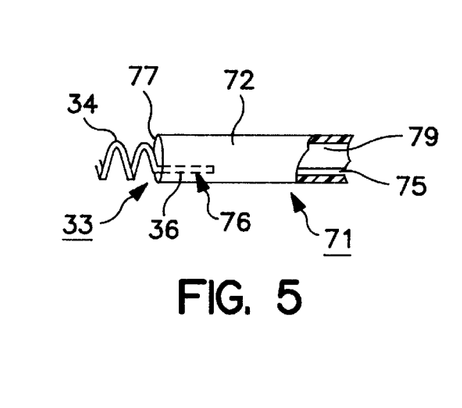
FIG. 5 is an enlarged, partial section view of the distal end of the arrangement of FIG. 3.

As shown in FIGS. 3 and 5, the distal pusher body end 69 is coupled with cardiac lead engaging means 71 for engaging the cardiac lead body 12 at or adjacent the distal lead end 33 to advance the distal lead end 33 when the pusher body 62 is advanced and for disengaging from the cardiac lead 12 when the pusher body 62 is withdrawn. The cardiac lead engaging means 71 extends distally from the distal pusher body end 69 and engages cooperative engagement means 36 at the distal lead end 33 such that the lead body 12 is advanced distally through the transvenous path and to the cardiac implantation site in the heart chamber or cardiac blood vessel as force is applied to the proximal pusher end handle 64 and the proximal segment of pusher body 62 extending outside the incision in the patient's body. The cardiac lead engaging means 71 is configured to disengage from the cooperative engagement means 36 at the distal lead end 33 simply upon retraction or withdrawal of the pusher body 12 proximally through the patient's vascular system.

Figure 7:
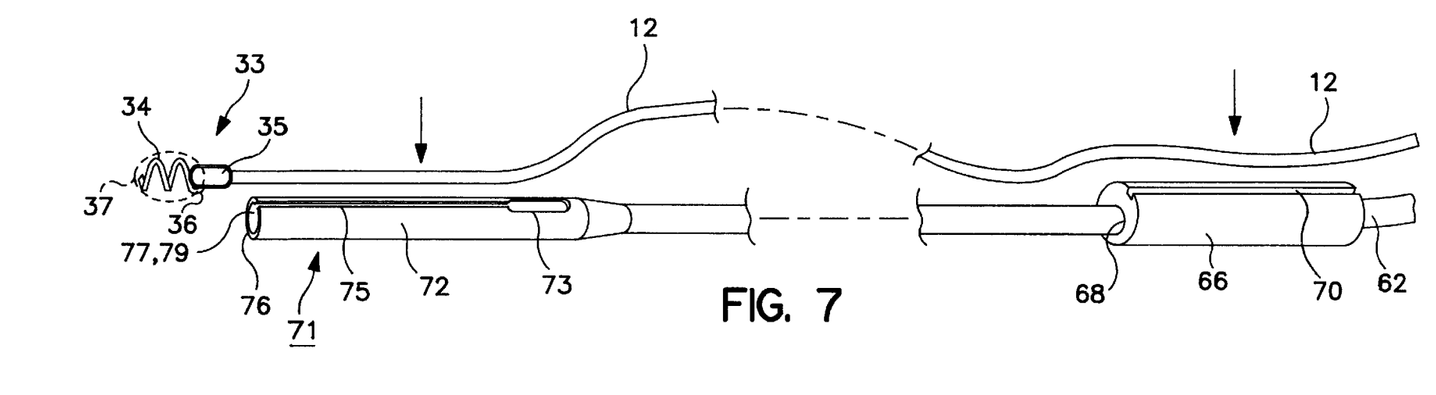
FIG. 7 is an illustration of the alignment and insertion of the lead body of the cardiac lead into the cardiac lead engaging means and lead body retainer of FIG. 3.
Figure 8:
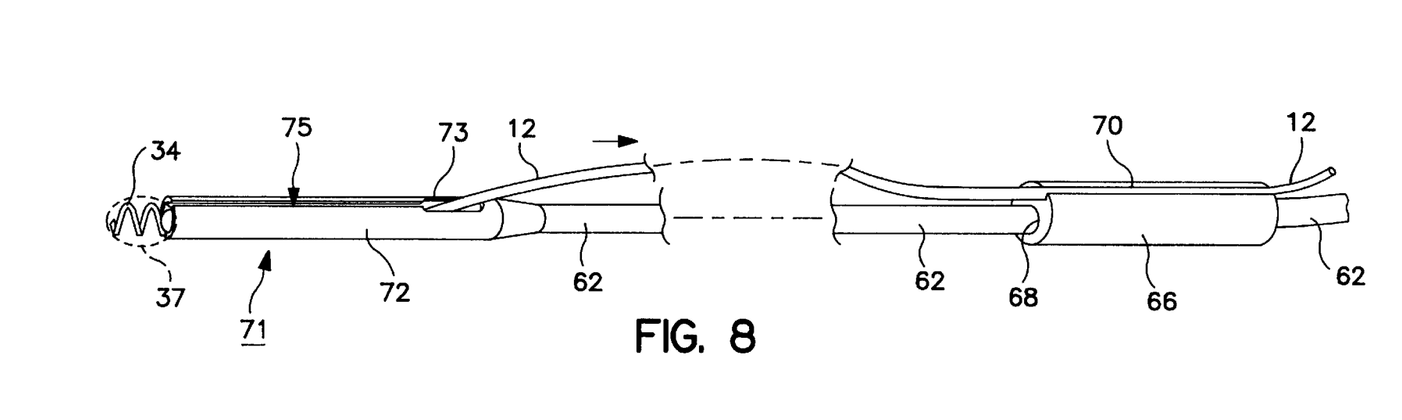
FIG. 8 is an illustration of the seating of the cooperative engagement key into the lead retention slot upon retraction of the lead body.

In a preferred embodiment also illustrated in FIGS. 7 and 8, the cardiac lead engaging means 71 includes a tubular sleeve 72 attached at a proximal sleeve end with the distal pusher body end 69. The tubular sleeve 72 has a side wall extending between a proximal sleeve side wall lumen opening 73 in the side wall and a distal sleeve lumen end opening 77. The tubular sleeve side wall surrounds a sleeve lumen 79 for receiving the distal lead end 33 as shown in FIGS. 3, 5 and 8. The tubular sleeve 72 is formed with an insertion slot or breech 75 extending between the proximal sleeve side wall lumen opening 73 and the distal sleeve lumen end opening 77. The insertion breech 75 is wide enough or can be stretched wide enough to allow the lead body 12 proximal to the distal lead end 33 to be laterally inserted therethrough as shown in FIG. 7, leaving the distal lead end 33 including the helical electrode 34 extending distally from the distal sleeve lumen end opening 77 as shown in FIGS. 3, 5 and 8.

The tubular sleeve 72 further comprises a lead retention slot 76 extending proximally in the sleeve side wall from the distal sleeve lumen end opening 77 that receives and engages a compatibly shaped cooperative engagement member or key 36 of the distal lead end 33. After the lead body 12 is laterally inserted through the breech 75 as shown in FIG. 7 and is within the sleeve lumen 79 as shown in FIG. 8, the distal lead end 33 extending distally from distal sleeve lumen end opening 77 is rotated to align cooperative engagement key 36 of the distal lead end 33 with the lead retention slot 76. At least a proximal portion of the distal lead end 33, including the enlarged crimp zone 35 and the cooperative engagement key 36, is seated in the tubular sleeve lumen 79 by retracting the lead body 12 proximally through the proximal sleeve side wall lumen opening 73 as shown in FIG. 8. The cooperative engagement key 36 is seated into the lead retention slot 76 when the lead body 12 and lead distal end 33 are retracted as shown in FIGS. 3, 5, and 8,. The mutual engagement of key 36 in slot 76 prevents the distal lead end 33 from being released laterally through the breech 75 or from retracting further into the tubular sleeve lumen 79 during advancement of the pusher body 62. This mutual engagement also allows the distal lead end 33 to be rotated by rotation of the pusher body 62 and the lead body 12 by manipulation of the pusher body handle 64 and lead body 12 extending outside the incision in the patient's skin. The disengagement of the cooperative engagement member or key 36 from the lead retention slot 76 can be effected by simply retracting the pusher body handle 64 outside the incision.

In this embodiment, the cooperative engagement key 36 comprises a shank of the helical electrode 34 that extends radially from the crimp zone 35 and then distally in a straight section as shown in FIG. 7. The lead retention slot 76 is wider and longer than the straight section width and length of the shank. The shank and lead retention slot 76 can take the shapes of the crank portion 80 and coupler 43 of the above-incorporated, commonly assigned '014 patent and include the protection against over rotation of the helix disclosed therein.

Figure 4:
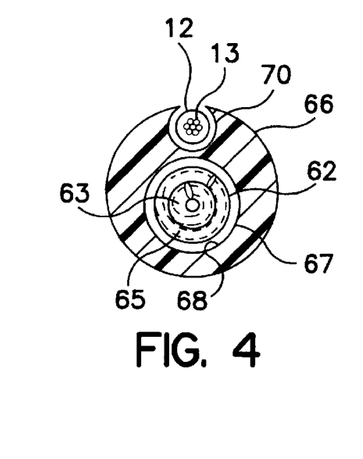
FIG. 4 is a cross-section view of the arrangement of FIG. 3 taken along lines 4—4 of FIG. 3.

The cardiac lead body 12 is preferably retained alongside the pusher body 62 by one or more lead retainer 66 located along the length of and fixed to the pusher body 62 as shown in FIGS. 3, 4, 7 and 8. Each lead retainer 66 is formed with a retainer lumen 68 fitted around the pusher body 12 as shown in FIG. 4 to attach it thereto. Each lead retainer 66 also has an elongated lead body receiving slot 70 extending in parallel to the retainer lumen 68 that is dimensioned with respect to the lead body diameter to receive the lead body 12 therein when it is laterally inserted in breech loading fashion as shown in FIG. 7. After the lead body 12 is inserted into the elongated lead body receiving slot 70, it is loosely retain therein as shown in FIG. 4. The lead body 12 is thereby maintained extending alongside the pusher body 62 during advancement through the transvenous path. The lead retainer 66 facilitates the twisting and rotation of the arrangement of the lead pusher 60 and the cardiac lead 10 from the proximal ends thereof. After the cardiac electrode (s) are located at the cardiac implantation site, the pusher body 62 is withdrawn proximally and each lead body receiving slot 70 slides along the lead body 12. The lead body 12 is laterally withdrawn from each lead body receiving slot 70 by the physician when each lead retainer 66 is withdrawn from the skin incision.

FIGS. 9–13 illustrate the steps of employing the arrangement of the first embodiment of the invention to guide and implant an endocardial cardiac lead having a distal fixation mechanism, e.g., distal helical electrode 34, at a selected cardiac implantation site. After the distal lead end 33 is seated as shown in FIGS. 7 and 8, and the arrangement is advanced to the implantation site, the entire arrangement is rotated by rotating the proximal lead body and connector end assembly 32 and the proximal pusher body handle 64 extending outside the patient's body to screw the helical electrode 34 into the myocardium. Then, the tubular sleeve 72 and pusher body 62 is retracted over the lead body 12 through the transvenous path and from the incision, and the lead body 12 is withdrawn from each lead body receiving slot 70 of each lead retainer 66.

Figure 9:
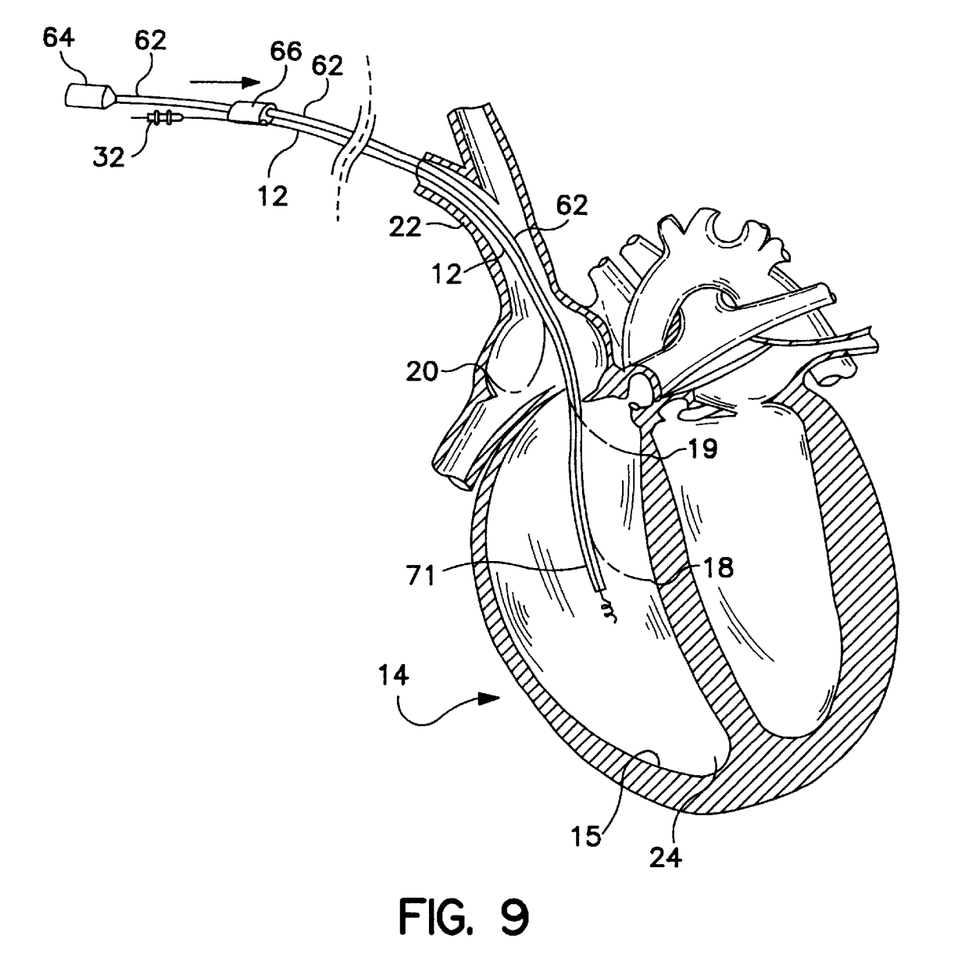
FIG. 9 is a schematic representation of the advancement of the arrangement of FIG. 3 through an incision in the patient's skin and the patient's vasculature and into the right ventricle in order to fix the distal helical electrode at one of the several illustrated cardiac implantation sites of the right ventricle.
Figure 10:
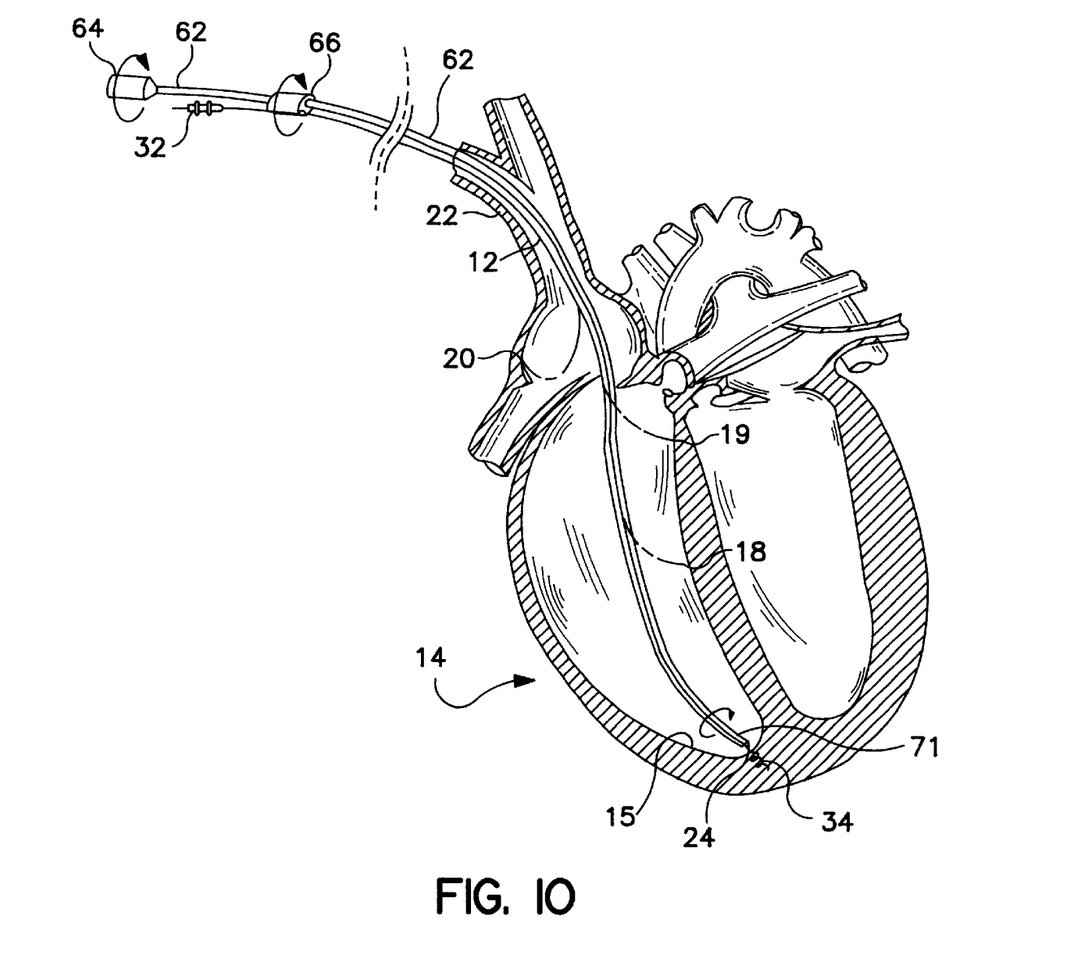
FIG. 10 is a schematic representation of the rotation of the arrangement of FIG. 3 from outside the incision in the patient's skin to impart rotational torque to the distal helical electrode to screw it into the myocardium at the apex of the right ventricle.
Figure 11:
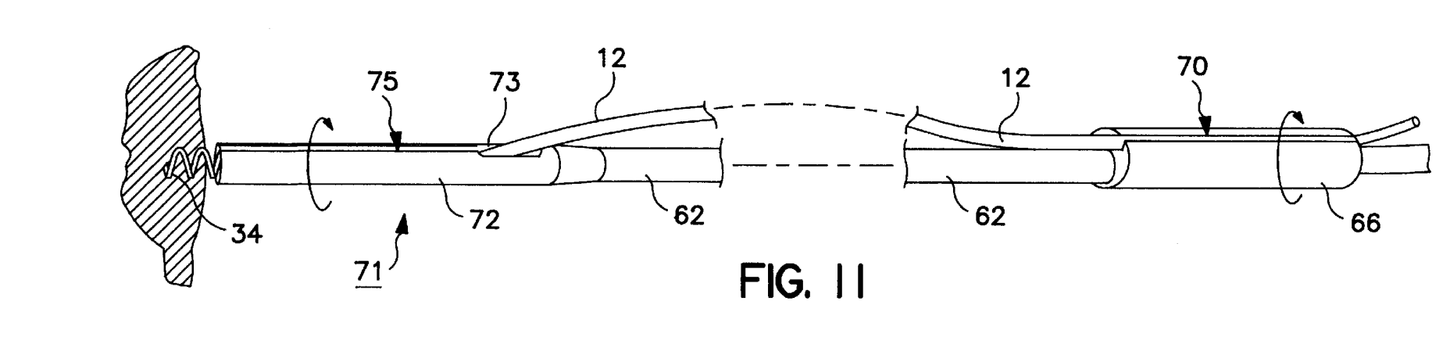
FIG. 11 is an enlarged view of the application of the rotational torque to the distal helical electrode and the lead body restrained in the lead body retaining slot shown in FIG. 10 showing how the lead body is rotated with the pusher body.

FIG. 9 is a schematic representation of the advancement of the arrangement of FIG. 3 through an incision in the patient's skin and the patient's vasculature and into the RV in order to fix the distal helical electrode 34 at one of the several illustrated cardiac implantation sites of the RV. The distal lead end 33 is seated in the sleeve tubular 72 and the arrangement is advanced to the implantation site. FIG. 10 is a schematic representation of the rotation of the arrangement of FIG. 3 from outside the incision in the patient's skin to impart rotational torque to the distal helical electrode 34 to screw it into the myocardium at the apex of the RV. FIG. 11 is an enlarged view of the application of the rotational torque to the distal helical electrode 34 and the lead body 12 restrained in the lead body retaining slots 70 shown in FIG. 10 showing how the lead body 12 is rotated with the pusher body 62. The entire arrangement is rotated from the proximal lead body end and the proximal pusher body handle extending outside the patient's body to screw the helical electrode 34 into the myocardium.

Figure 12:
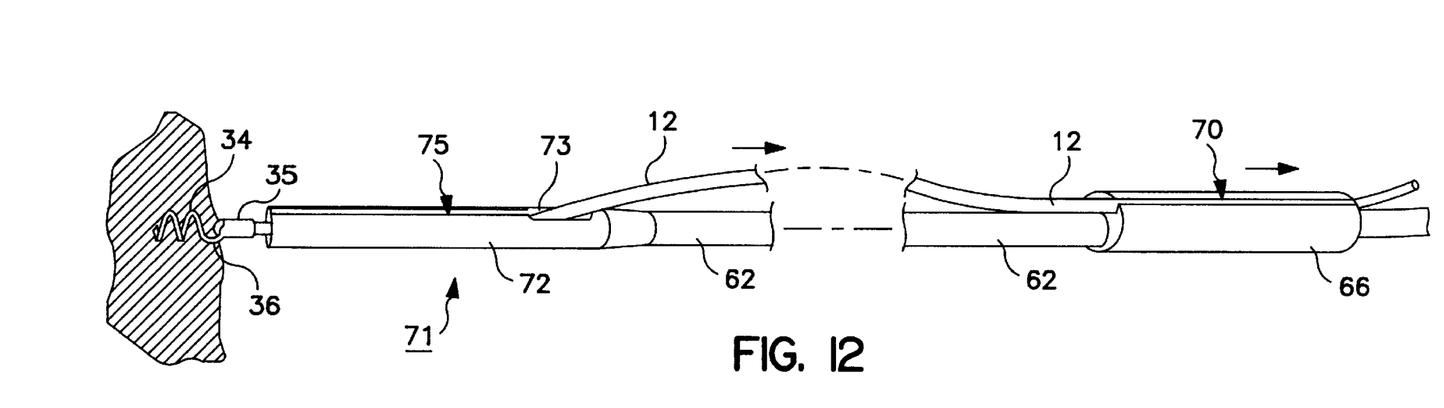
FIG. 12 is a schematic representation of the withdrawal of the lead pusher of FIG. 3 over the lead body by withdrawal force applied outside the incision to the pusher body.
Figure 13:
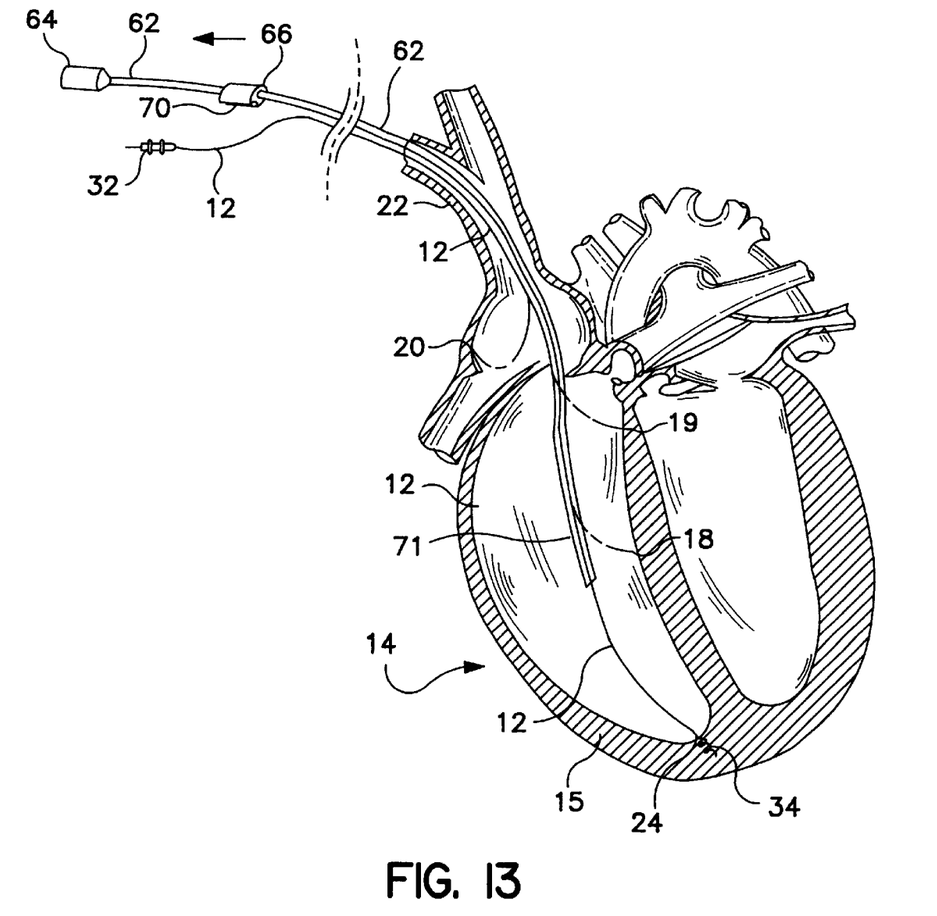
FIG. 13 is an enlarged view of the application of the withdrawal force to withdraw the lead pusher over the lead body.
Figure 14:
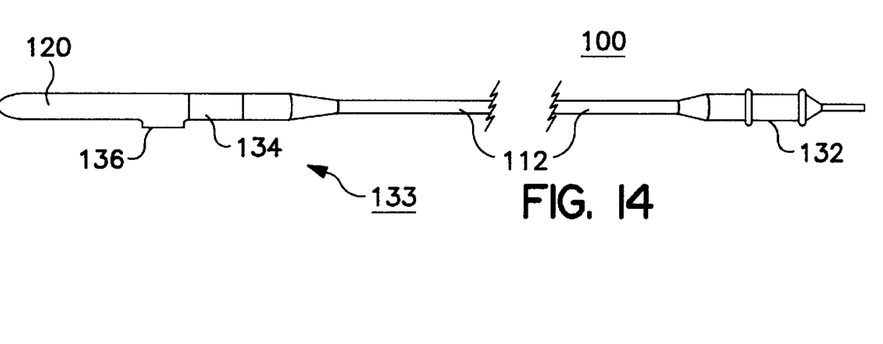
FIG. 14 is a plan view of a coronary sinus lead modified to be advanced by a lead pusher in accordance with a second embodiment of the invention.

FIG. 12 is a schematic representation of the withdrawal of the lead pusher 60 of FIG. 3 over the lead body by withdrawal force applied outside the incision to the pusher body 62. FIG. 13 is an enlarged view of the application of the withdrawal force to withdraw the lead pusher over the lead body. Each lead body receiving slot 70 and proximal sleeve side wall lumen opening 73 slides over the lead body 12 as the lead pusher 60 is withdrawn through the incision in the patient's skin. The lead body 12 is withdrawn laterally from each lead body receiving slot 70 of each lead retainer 66 after it is withdrawn through the incision.

The second preferred embodiment of the invention for introducing a CS endocardial cardiac lead 100 to one of the implantation sites depicted in FIG. 2 is depicted in FIGS. 14–18. The CS lead 100 is formed with a lead body 112 and lead connector end assembly 132 that is substantially the same as the lead body 12 and lead connector end assembly 32 described above. The CS lead distal end 133 is formed with a tapered distal extension 120 that is tapered to be advanced into the CS and through the great vein and cardiac vessels branching therefrom in a manner well known in the art. A cooperative engagement shoulder or key 136 is formed extending outward of the circumference of the tapered distal end just distal to a ring-shaped cardiac electrode 134. The cooperative engagement shoulder or key 36 is dimensioned to extend radially outwardly of the enlarged diameter distal lead end 33 and with a width and length that allows it to fit within the lead retention slot 76.

Figures 15, 16, 17:
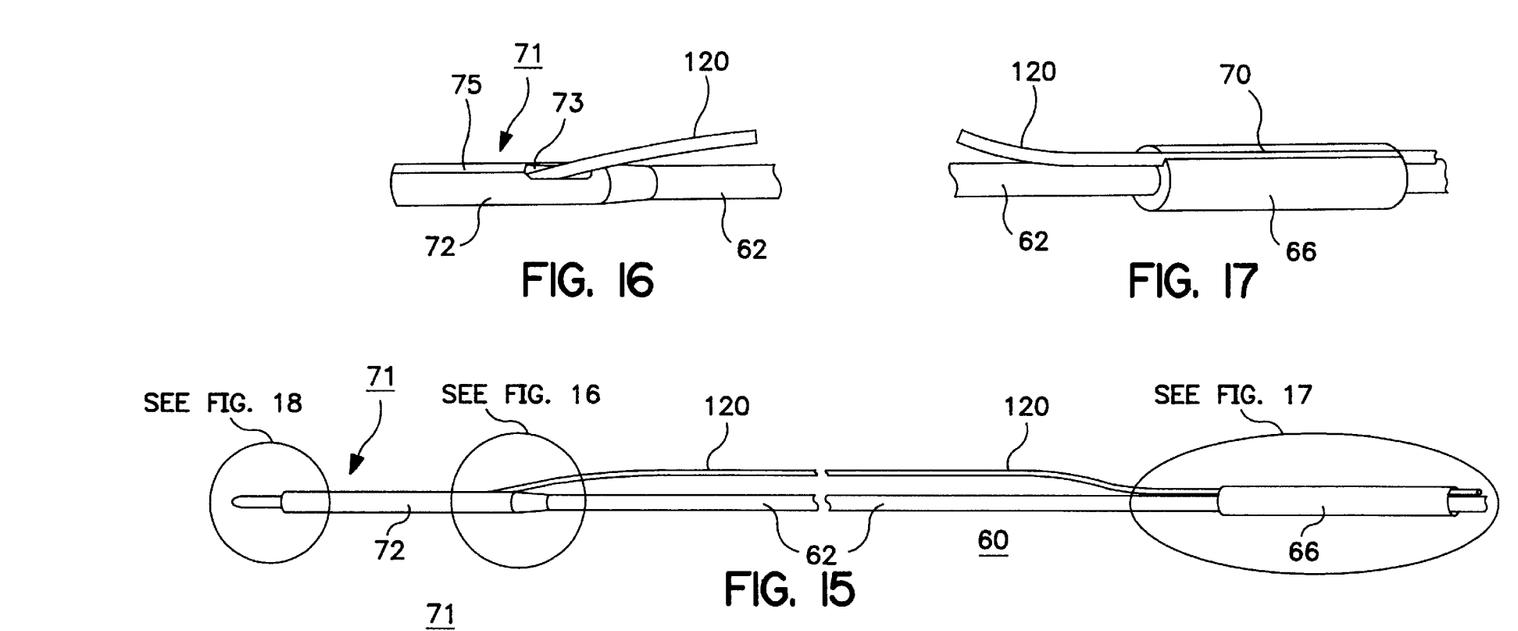
FIG. 15 is a plan view of the introduction arrangement of the second embodiment of the invention for introducing an endocardial cardiac lead of the type illustrated in FIG. 14 to a cardiac blood vessel implantation site depicted in FIG. 2.
FIG. 16 is an enlarged, partial section view of the cardiac lead engaging means of the arrangement of FIG. 15.
FIG. 17 is an enlarged, partial section view of the lead body and lead body retainer of the arrangement of FIG. 15.
Figure 18:
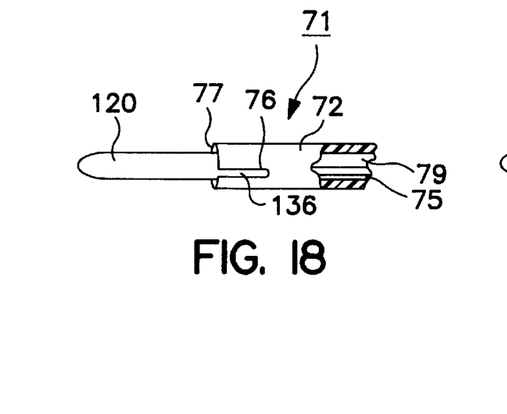
FIG. 18 is an enlarged, partial section view of the distal end of the arrangement of FIG. 15.

The lead pusher 60 is constructed substantially the same as the lead pusher 60 described above. The lead body 112 is adapted to be laterally inserted through the breech 75 and into the lead retention slot 70 as shown in FIGS. 15–17 in the manner described above. Similarly, the cooperative engagement shoulder or key 136 is fitted within the lead retention slot 76 as shown in FIG. 18 in substantially the same manner and following substantially the same steps as described above with reference to the first embodiment.

In the practice of this embodiment of the invention, the assembled arrangement of the CS lead 100 and lead pusher 60 shown in part in FIG. 15 is advanced to one of the LA or LV implantation sites of FIG. 2. Then, withdrawal force is applied outside the incision to the pusher body 62 to withdraw the lead pusher over the lead body 112. Each lead body receiving slot 70 and proximal sleeve side wall lumen opening 73 slides over the lead body 112 as the lead pusher 60 is withdrawn through the incision in the patient's skin. The lead body 112 is withdrawn laterally from each lead body receiving slot 70 of each lead retainer 66 after it is withdrawn through the incision.

The cooperative engagement key 136 may also be employed on distal lead ends of other types of endocardial cardiac leads including such leads having soft pliant tines for passive fixation.

In these preferred embodiments of the invention, the tubular sleeve 72 can have a length between 0.25 inches and 2.5 inches, and preferably about 0.75 inches. The material and thickness of the tubular sleeve is selected to provide sufficient rigidity to perform the above identified tasks without unduly stiffening the distal end of the lead pusher 60. Bends and curves can be imparted into the pusher body 62 just proximal to the tubular sleeve 72 to enhance the ability to traverse the transvenous pathway and cardiac blood vessels.

The cooperative engagement shoulder or key 136 and lead retention slot 76 can take other forms than those shown in the drawings as long as the ability to advance the lead through the patient's vasculature and into the CS and great vein to the cardiac implantation sites depicted in FIG. 2 is preserved. In a further variation of the second embodiment, the tubular sleeve can be shortened considerably and the lead retention slot 76 eliminated. In this variation, the lead body is formed with one or more outwardly projecting cooperative engagement key 136 which each act as a shoulder against which the tubular sleeve bears. The tubular sleeve comprises a lead body receiving loop which can be manually adjusted between an open position for providing the breech for laterally receiving the lead body proximal to the shoulder and a closed position sufficient to retain and slidingly engage with the lead body. The lead body receiving loop or sleeve bears against the shoulder that prevents it from passing distally over the distal lead end during advancement of the arrangement through the patient's vasculature and into the heart chamber or cardiac vessel. The cardiac lead is pulled along by this cooperative engagement as the pusher body is advanced distally through the transvenous path into the heart chamber or cardiac blood vessel. After the electrode is located at the cardiac implantation site, the pusher body can be withdrawn proximally along the lead body until the lead body receiving loop or sleeve exits the skin incision where it can be opened to release the lead body.

While particular embodiments of the invention have been disclosed herein in detail, this has been done for the purposes of illustration only, and is not intended to limit the scope of the invention as defined in the claims which follow. It is to be understood that various substitutions, alterations, or modifications can be made to the disclosed embodiment without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

What is claimed is:

1. An arrangement to facilitate the introduction and advancement of an endocardial cardiac lead, comprising:

an endocardial cardiac lead including a lead body having a lead body diameter and extending between a proximal lead end and a distal lead end, a lead conductor extending within said lead body between said proximal and distal lead ends, and a cardiac electrode at or adjacent said distal lead end electrically connected to said lead conductor;

pusher means for engaging and advancing said cardiac lead transvenously, said pusher means further comprising:

an elongated pusher body having a pusher body exterior surface and extending between a proximal pusher body end and a distal pusher body end and formed of flexible material having sufficient column strength to be advanced transvenously with the cardiac lead body extending alongside said pusher body exterior surface; and cardiac lead engaging means coupled with said distal pusher body end for engaging the cardiac lead at or adjacent the distal lead end while said lead body extends alongside said pusher body exterior surface; and wherein said lead comprises cooperative engagement means formed at said distal lead end of said cardiac lead for engaging with said cardiac lead engaging means responsive to force applied to the pusher body to advance said pusher body distally and for disengaging from said cardiac lead engaging means at said distal lead end responsive to retraction of the pusher body proximally.

2. The arrangement of claim 1, wherein said pusher body is a torque cable.

3. The arrangement of claim 1, wherein said pusher body is rod or wire shaped and said cardiac lead engaging means is a tubular sleeve having a side wall surrounding a sleeve lumen extending between a proximal sleeve lumen opening and a distal sleeve lumen opening and formed to receive said distal lead end.

4. The arrangement of claim 3, wherein said pusher body is a torque cable.

5. The arrangement of claim 3, wherein said pusher body is a torque cable coated with an elastomeric compound.

6. The arrangement of claim 3, wherein said pusher body is coated with an elastomeric compound.

7. The arrangement of claim 1, wherein:

said cooperative engagement means comprises a shaped portion of said distal lead end; and said cardiac lead engaging means formed at said distal pusher body end is of a shape which interlocks with said shaped portion of said distal lead end to allow said distal lead end to be advanced with advancement of said pusher body distally and to allow said shaped portion to disengage from said cardiac lead engagement means upon retraction of the pusher body and tubular sleeve proximally.

8. The arrangement of claim 7, further comprising at least one lead retainer located along the length of and fixed to said pusher body intermediate said proximal pusher body end and said distal pusher body end, each lead retainer having a lead body receiving slot that is dimensioned with respect to said lead body diameter to receive and loosely retain said lead body alongside said pusher body.

9. The arrangement of claim 1, wherein:

said pusher body is rod or wire shaped; and said cardiac lead engaging means extends distally from said rod or wire shaped distal pusher body end and further comprises:

a tubular sleeve having a side wall surrounding a sleeve lumen extending between a proximal sleeve lumen opening and a distal sleeve lumen opening, said sleeve lumen dimensioned to receive said distal lead end therein; and retention means engageable with said cooperative engagement means of said distal lead end in said sleeve lumen, for preventing said distal lead end from retracting proximally and out of said proximal sleeve lumen opening as said pusher body and said cardiac lead body are advanced distally and allowing said distal lead end to be released distally from said distal sleeve lumen opening upon retraction of said pusher body proximally.

10. The arrangement of claim 9, wherein said tubular sleeve is split to form a breech extending between said proximal sleeve lumen opening and said distal sleeve lumen opening having a breech width that is wide enough to allow a section of said lead body proximal to said distal lead end to be laterally inserted through said breech and into said sleeve lumen.

11. The arrangement of claim 10, wherein:

said cooperative engagement means comprises a shaped portion of said distal lead end; and said cardiac lead engaging means formed at said distal pusher body end is formed in said tubular sleeve in a shape which interlocks with said shaped portion of said distal lead end while said distal lead end is received in said sleeve lumen to allow said distal lead end to be advanced with advancement of said pusher body and to allow said shaped portion to disengage from said cardiac lead engagement means upon retraction of the pusher body and tubular sleeve.

12. The arrangement of claim 9, wherein:

said distal lead end is formed at least in part with a distal lead end side wall having a distal lead end diameter that exceeds said lead body diameter and said breech width and fits within said sleeve lumen;

said retention means comprises a lead retention slot extending proximally a predetermined distance in the sleeve side wall from the distal sleeve lumen opening; and said cooperative engagement means comprises a key extending outward of said distal lead end side wall and dimensioned to be received and seated in said lead retention slot following insertion of said lead body through said breech and into said sleeve lumen, alignment of said key with said lead retention slot, and retraction of said distal lead end into said distal sleeve lumen opening to draw said key into said lead retention slot.

13. The arrangement of claim 1, further comprising at least one lead retainer located along the length of and fixed to said pusher body intermediate said proximal pusher body end and said distal pusher body end, each lead retainer having a lead body receiving slot that is dimensioned with respect to said lead body diameter to receive and loosely retain said lead body alongside said pusher body.

14. A method of introducing and advancing the arrangement of claim 1 comprising:

fitting said cooperative engagement means formed at said distal lead end of said cardiac lead into engagement with said cardiac lead engaging means;

applying force to the pusher body to advance said pusher body and said cardiac lead body distally to a cardiac implantation site;

disengaging said cardiac lead engaging means from said lead cooperative engagement means; and retracting said pusher body.

15. An arrangement to facilitate the introduction and advancement of an endocardial cardiac lead, comprising:

an endocardial cardiac lead including a lead body having a lead body diameter and extending between a proximal lead end and a distal lead end, a lead conductor extending within said lead body between said proximal and distal lead ends, a cardiac electrode at or adjacent said distal lead end electrically connected to said lead conductor, and an active fixation helix extending distally from said distal lead end;

pusher means for engaging and advancing said cardiac lead transvenously, said pusher means comprising:

an elongated pusher body having a pusher body exterior surface and extending between a proximal pusher body end and a distal pusher body end formed of flexible material having sufficient column strength to be advanced transvenously with the cardiac lead body extending alongside said pusher body exterior surface;

cardiac lead engaging means coupled with said distal pusher body end for engaging the cardiac lead at or adjacent the distal lead end while said lead body extends alongside said pusher body exterior surface; and wherein said lead comprises cooperative engagement means formed at the distal lead end thereof for engaging with said cardiac lead engaging means responsive to force applied to the pusher body to advance said pusher body distally and for transmitting torque to said helix and adapted to screw said helix into cardiac tissue upon rotation of said pusher body and for disengaging from said cardiac lead engaging means at said distal lead end upon retraction of the pusher body proximally.

16. The arrangement of claim 15, wherein:

said pusher body is rod or wire shaped; and said cardiac lead engaging means extends distally from said rod or wire shaped distal pusher body end and further comprises a tubular sleeve having a side wall surrounding a sleeve lumen extending between a proximal sleeve lumen opening and a distal sleeve lumen opening, said sleeve lumen dimensioned to receive said distal lead end therein.

17. The arrangement of claim 16, wherein:

said cooperative engagement means comprises a shank portion of said helix extending radially from said distal lead end and connecting said helix with said distal lead end; and said tubular sleeve further comprises retention means for engaging said shank portion in said sleeve lumen to prevent said distal lead end and helix from retracting proximally and out of said proximal sleeve lumen opening as said pusher body and said cardiac lead body are advanced proximally and transmitting torque to said helix upon rotation of said pusher body end and allowing said distal lead end to be released distally from said distal sleeve lumen opening upon retraction of said pusher body proximally.

18. The arrangement of claim 17, wherein said tubular sleeve is split to form a breech extending between said proximal sleeve lumen opening and said distal sleeve lumen opening having a breech width that is wide enough to allow a section of said lead body proximal to said distal lead end to be laterally inserted through said breech and into said sleeve lumen.

19. The arrangement of claim 18, wherein:

said distal lead end is formed at least in part with a distal lead end side wall having a distal lead end diameter that exceeds said lead body diameter and said breech width and fits within said sleeve lumen to present said helix extending distally from said distal sleeve lumen opening; and said retention means comprises a lead retention slot extending proximally a predetermined distance in the sleeve side wall from the distal sleeve lumen opening; and wherein:

said shank portion extends outward of said distal lead end side wall and is dimensioned to be received and seated in said lead retention slot following insertion of said lead body through said breech and into said sleeve lumen, alignment of said shank portion with said lead retention slot, and retraction of said distal lead end into said distal sleeve lumen opening to draw said shank portion into said lead retention slot.

20. The arrangement of claim 15, further comprising at least one lead retainer located along the length of and fixed to said pusher body intermediate said proximal pusher body end and said distal pusher body end, each lead retainer having a lead body receiving slot that is dimensioned with respect to said lead body diameter to receive and loosely retain said lead body alongside said pusher body.

21. A method of introducing and advancing the arrangement of claim 18 comprising:

fitting said cooperative engagement means formed at said distal lead end of said cardiac lead into engagement with said cardiac lead engaging means;

applying force to the pusher body to advance said pusher body and said cardiac lead body distally to a cardiac implantation site;

transmitting torque to said helix to screw said helix into cardiac tissue;

disengaging said cardiac lead engaging means from said lead cooperative engagement means; and retracting said pusher body.

* * * * *